US009222893B2

(12) United States Patent
Hornabrook et al.

(10) Patent No.: US 9,222,893 B2
(45) Date of Patent: *Dec. 29, 2015

(54) MODIFIED APPARATUS AND METHOD FOR ASSESSMENT, EVALUATION AND GRADING OF GEMSTONES

(75) Inventors: Graham Alfred Hornabrook, New South (AU); Stuart Marchant, Alstonville (AU); Rodney Herbert Lummis, Tamworth (AU); Kathryn Elizabeth Primmer, Appin (AU); Angus Nelson Hornabrook, Clagiraba (AU); Peter Bruce Sutton, Dubbo (AU); Robert George Imrie, Gulargambone (AU); Leanne Bischof, Putney (AU); Ryan Lagerstrom, Stanmore (AU); Volker Hilsenstein, Toowong (AU)

(73) Assignee: OPAL PRODUCERS AUSTRALIA LIMITED, New South Wales (AU)

( * ) Notice: Subject to any disclaimer, the term of this patent is extended or adjusted under 35 U.S.C. 154(b) by 1125 days.

This patent is subject to a terminal disclaimer.

(21) Appl. No.: 13/123,260

(22) PCT Filed: Oct. 9, 2009

(86) PCT No.: PCT/AU2009/001332
§ 371 (c)(1),
(2), (4) Date: Sep. 2, 2011

(87) PCT Pub. No.: WO2010/040180
PCT Pub. Date: Apr. 15, 2010

(65) Prior Publication Data
US 2011/0310246 A1    Dec. 22, 2011

(51) Int. Cl.
*G01N 21/87* (2006.01)
*G01N 33/38* (2006.01)
(Continued)

(52) U.S. Cl.
CPC .............. *G01N 21/87* (2013.01); *G01N 33/381* (2013.01); *G06K 9/4652* (2013.01);
(Continued)

(58) Field of Classification Search
CPC ............... G01J 3/46; G01J 3/463; G01J 4/00; G01J 5/08; G01N 33/381; G01N 2223/05; G01N 2223/052; G01N 21/87; G06K 9/46; G06K 9/4642; G06K 9/4652; G06K 9/4661
See application file for complete search history.

(56) References Cited

U.S. PATENT DOCUMENTS

| 6,239,867 B1 | 5/2001 | Aggarwal |
| 6,508,009 B1 | 1/2003 | Tubis et al. |

(Continued)

FOREIGN PATENT DOCUMENTS

| WO | WO 01/61316 A1 | 8/2001 |
| WO | WO 03/062942 A2 | 7/2003 |

OTHER PUBLICATIONS

International Preliminary Report on Patentability (IPRP), Aug. 9, 2010.

*Primary Examiner* — Manav Seth
(74) *Attorney, Agent, or Firm* — Abelman, Frayne & Schwab

(57) ABSTRACT

An apparatus (10) for assessment, evaluation and grading of gemstones has a stage (11) upon which a gemstone may be supported. The stage is enclosed in a housing (15) that is impervious to light. There is at least one light source (14) located in the housing which is adapted to project incident light onto the gemstone. Means for rotating and tilting the stage so as to vary the orientation of the gemstone to the incident light are also present. A digital camera (16) is located in the housing adjacent the or each light source and is adapted to take images of the gemstone based on reflection and/or refraction of the incident light. The apparatus also includes information processing means for calibrating and analyzing the images. The information processing means is programmed with instruction sets for assessing one or more of color, cut, clarity, scintillation, brilliance, lustre, dispersion and sheen. The gemstone is supported upon the stage by securing means (17) engaging the gemstone at its bottom surface.

7 Claims, 9 Drawing Sheets

(51) Int. Cl.
   *G06K 9/46* (2006.01)
   *G01J 3/46* (2006.01)
   *G01J 4/00* (2006.01)
   *G01J 5/08* (2006.01)

(52) U.S. Cl.
   CPC .............. *G06K 9/4661* (2013.01); *G01J 3/463* (2013.01); *G01J 4/00* (2013.01); *G01J 5/08* (2013.01); *G01N 2223/05* (2013.01)

(56) References Cited

U.S. PATENT DOCUMENTS

| | | | |
|---|---|---|---|
| 6,980,283 B1 * | 12/2005 | Aggarwal | 356/30 |
| 7,259,839 B2 * | 8/2007 | Sivovolenko | 356/30 |
| 7,336,347 B2 * | 2/2008 | Sasian et al. | 356/30 |
| 7,355,683 B2 * | 4/2008 | Sasian et al. | 356/30 |
| 7,372,552 B2 * | 5/2008 | Sasian et al. | 356/30 |
| 7,382,445 B2 * | 6/2008 | Sasian et al. | 356/30 |
| 7,388,656 B2 * | 6/2008 | Liu | 356/30 |
| 7,420,657 B2 * | 9/2008 | Sasian et al. | 356/30 |
| 7,571,060 B2 * | 8/2009 | Blodgett et al. | 702/35 |
| 7,751,034 B2 * | 7/2010 | Sasian et al. | 356/30 |
| 8,095,325 B2 * | 1/2012 | Blodgett et al. | 702/35 |
| 8,116,552 B2 * | 2/2012 | Lapa et al. | 382/141 |
| 8,239,143 B2 * | 8/2012 | Blodgett et al. | 702/35 |
| 8,317,521 B2 * | 11/2012 | Lapa et al. | 434/386 |
| 8,402,066 B2 * | 3/2013 | Verboven et al. | 707/802 |
| 8,436,986 B2 * | 5/2013 | Hornabrook et al. | 356/30 |
| 8,705,018 B2 * | 4/2014 | Benderly et al. | 356/30 |
| 8,834,177 B2 * | 9/2014 | Lapa et al. | 434/386 |
| 2005/0036132 A1 | 2/2005 | Lapa et al. | |
| 2008/0188961 A1 * | 8/2008 | Marcum | 700/89 |
| 2010/0111354 A1 * | 5/2010 | Hornabrook et al. | 382/100 |

* cited by examiner

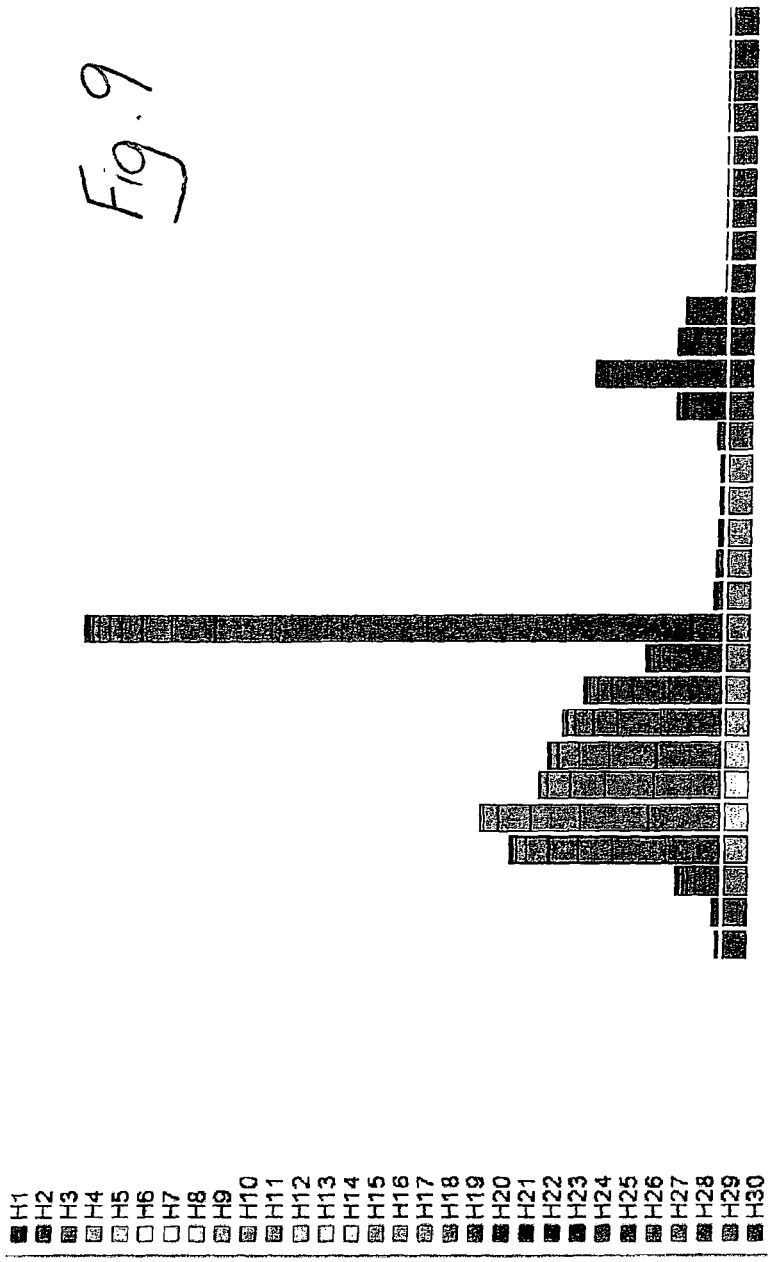

MODIFIED APPARATUS AND METHOD FOR ASSESSMENT, EVALUATION AND GRADING OF GEMSTONES

TECHNICAL FIELD

The present invention relates to apparatus and methods for assessment, evaluation and grading of gemstones (including inorganic and organic gemstones) and minerals, such as opals, pearls and diamonds, as well as mineral specimens. In particular, the present invention relates to a digital analyser for such gemstones and minerals which incorporates both hardware and software.

Although the background of the invention and the preferred embodiments of the invention will be hereinafter described with reference to the assessment, evaluation and grading of opals and other coloured gemstones, it will be apparent to persons skilled in the art that it is the intent of this specification that the invention described herein be not limited thereto, but have wider application to all gemstones and minerals. For ease of understanding in this specification, the term "gemstones(s)" will be used when referring to all gemstones and minerals that fall within the scope of the invention.

The present invention also relates to apparatus and method for assessment, evaluation and grading of certain gemstones that have both faceted and/or cabochon surfaces, such as opals, diamonds, sapphires, rubies, emeralds, aquamarine and alexandrite. For ease of reference in this specification, such gemstones are to be hereinafter referred to as "coloured gemstones".

BACKGROUND ART

Current opal assessment and evaluation practices are highly subjective as they are based on a combination of human observed factors, such as scoring the flashes of colour as the opal is moved, the body tone, colour, brightness and pattern. The fact that Australia contributes 95% of the world's opals is both a blessing and a curse. Overseas buyers often do not have the training to assess the value of opals being supplied (leading to difficult negotiations between buyer and seller), nor can they describe a particular type of opal in sufficiently concise and objective terms for the suppliers to be able to provide the appropriate opals.

Most gemstone assessment is made using a magnification 10× loupe. The gemstone is observed by holding it in a pair of gemstone tweezers and turning it (using pitch, roll and yaw) to observe light interaction with the gemstone and external and internal characteristics.

The subjective nature of current opal assessment and evaluation practices creates difficulty in negotiations and substantial distortions in the terms of trade between the opal miners and the buyers.

There exist a number of key characteristics on which an opal can be graded for its value, such as:
  Colour (hue) and area of flash
  Brightness
  Body tone
  Pattern
  Shape
  Other characteristics In terms of relative importance to the overall gemmological value of an opal, colour and body tone combined have about a 40% weighting, followed by brightness and pattern, each at about 30%, with the remaining characteristics being of much less significant weighting. In terms of seeking an objective assessment by a human observer, colour appears to be the most difficult, followed by brightness, which seems easier to assess and quantify manually, as is the pattern, of which there are 28 main types.

Colour is difficult for a human observer to assess because of the following:

(1) The contribution of each colour changes with viewing angle, that is, with pitch, roll and yaw. All orientations are to be integrated in a colour estimation, which is difficult due to the limited perception and subjective memory of humans and their eyesight variables.

(2) Out in the field, it is difficult to accurately assign a shade according to a colour reference chart because the conditions for viewing are highly variable.

To compound the problem, synthetic or man-made replicas of opals and other gemstones are improving, and in some cases (eg diamonds), it is extremely difficult to detect the natural gemstone from the synthetic. Verifying the authenticity of the gemstones is another problem that may be resolved by adoption of objective and automated analytical methods.

One approach to provide an objective and automated analytical method and image capture device for the grading of diamonds is disclosed in U.S. Pat. No. 6,239,867 ("the Patent"). Although also referring to use of the method and device for the grading of opals and other gemstones, that approach is unsuited to opals and is poorly suited to other gemstones, even diamonds. The image capture device and method disclosed in the Patent do not allow for gemstone movements of pitch, roll and yaw during the capture of images so as to display the "play of colours" of the gemstone, as the gemstone stage is not tiltable. Nor does the Patent disclose the assessment of all segments of the face of a gemstone for each of colour, brightness, body tone and other characteristics, many of which are especially important for opals, before grading the gemstone for each characteristic. Rather, the Patent discloses a method of sampling a small area of a diamond by moving a camera through a controlled arc and averaging the total illumination data in that area to assess the colour of the diamond.

Such a limited sampling is not suited to opals as it will not display the "play of colours", body tone and brightness of an opal over all segments. In particular, the Patent states that gemstone colour analysis is done by obtaining average red, green and blue (RGB) values for colour images in the image pixel region delineated by the girdle and the table facets, and that by sampling the colour of a smaller region a more predictable and accurate colour reading is obtained. These procedures are not suited to the assessment of opals, where it is the entire face of the opal that requires colour assessment.

Furthermore, the image capture device disclosed in the Patent filters the light between the gemstone and its camera, and this is stated to be critical to the analysis of colours. That device also uses high viscosity immersion oil either between the gemstone and a glass plate upon which it is centrally placed or to immerse the gemstone so as to remove glint and assist in the transmission of light though the gemstone for the detection of flaws or colour inclusions. These features of the image capture device and method disclosed in the Patent are unsuited to opals and are poorly suited to other gemstones.

The beauty of coloured gemstones depends entirely on their effect on light. Factors attributing to the assessment of a gemstone will include colour, changing colour patterns, transparency, lustre and brilliance, dispersion and "fire".

Coloured gemstones are separated into crystal systems defined by their atomic structure, geometric form as an expression of the atomic structure, and the relationship between the structure and physical properties.

Each crystal system has defined optical properties. They can be:
- singly refractive—(isotrophic) where a refracted ray travels in a single new direction at a constant new velocity
- doubly refractive—(anisotrophic) where a light ray is refracted and split into two rays which take different paths and proceed with different velocities, the medium having more than one refractive index
- doubly refractive uniaxial—where such a medium possesses one direction parallel to which the two split rays appear to be isotrophic—the optic axis
- doubly refractive biaxial—where such a medium possesses two directions parallel to which the two split rays appear to be isotrophic.

The following Table identifies the various geometric forms that different crystal systems take:

| Crystal System | Examples | Optical Character |
| --- | --- | --- |
| Cubic | diamond, garnet, spinel | Isotrophic |
| Tetragonal | zircon, scapolite | Anisotrophic Uniaxial |
| Hexagonal | emerald, apatite | |
| Trigonal | Sapphire, ruby, tourmaline | |
| Orthorhombic | Topaz, peridot | Anisotrophic Biaxial |
| Monoclinic | Kunzite, moonstone | |
| Triclinic | Sunstone | |

Coloured gemstones are further defined by their chemical composition and trace elements which affect colours produced and the behaviour of light, both reflected and refracted, and are identified by their optical properties, specific gravity, hardness, inclusions and colour using various known instruments. Such instruments include:
- 10× hand lens—used for routine observation of gemstones
- Refractometer—measures the refractive index of light emitted through the stone
- Dichroscope—shows two colours present in a doubly refractive stone
- Polariscope—determines the optical character of the stone—doubly or singly refractive, and assists to find the various crystal axis of the stone
- Microscope—analysis of internal characteristics by extended magnification
- Specific gravity—displacement measurement in water
- Chelsea filter—allows transmission of both deep red wavelengths around 690 nm and yellow-green wavelengths, around 570 nm, that matches emerald's emission and absorption characteristics, recommended to assist the discrimination between natural emerald and its simulants such as green glass, tourmaline and peridot.
- Spectroscope—measures the spectral emission and interference wavelengths
- SW/LW UV light box—measures the stone's reaction to UV light—fluorescence and phosphorescence.

Coloured gemstones are assessed on the quality of light refracted and reflected—brightness and saturation of colour, inclusions present, quality of cut and carat weight; the four "C"s as noted by the diamond industry—colour, cut, clarity and carat weight.

Coloured gemstones have faceted surfaces in various shapes—round, rectangle, square, pear, heart, triangular being more common (virtually any shape is now possible particularly with laser cutting), cut and polished en cabochon—oval or round, beads or tumbled, carved and freeform shapes.

Almost any colour can be found among gemstones, and the uncut minerals from which they are derived. Some species show a wide range of colour whereas others are constant.

Gemstones are coloured by the selective absorption of light—the interaction between light waves and electrons and/or structural colouring. For idiochromatic (self coloured) minerals, their colour is a fundamental property, constant and characteristic of that mineral and the colour is due to the major chemical composition of the mineral. When the colour arises from a trace impurity in the basic chemical composition, the mineral is called allochromatic (other coloured).

Pleochroism or dichroism is the change in colour evident as the mineral is rotated under plane-polarized light. The primary cause of dichroism or pleochroism in minerals is due to adsorption of particular wavelengths of light. This selective adsorption of certain wavelengths of light causes the transmitted light to appear coloured. This colour is a function of the thickness and the particular chemical and crystallographic nature of the mineral. If the adsorption of particular wavelengths of light differs according to the optical path, the phenomena of pleochroism is evident. This is observable in plane-polarized light when the polarizers select the light exiting from the mineral. This colour depends on which optical path is viewed. Pleochroic colours are observed and recorded in the mineral data and are generally diagnostic of the particular mineral.

Coloured gemstones exhibit various degrees of transparency, these being:
- transparent—an object viewed through the stone shows outlines clearly and distinctly
- a translucent—some light passes through but no object can be seen through the stone
- opaque—no light passes through Lustre is a basic essential character of cut and polished gemstones. Lustre imparts life and brilliance and has much to do with their beauty. Lustre is purely an external surface effect and depends on the amount and quality of reflected light from the surface of the gemstone.

The various types of lustre are described in the following Table:

| Lustre | Description | Example |
| --- | --- | --- |
| Adamantine | Hard and brilliant | Diamond |
| Vitreous | Like broken glass | Emerald, ruby |
| Resinous | As resin | Amber, opal, some garnets |
| Waxy | Seems covered with a thin layer of oil. Can result from the scattering of light by a microscopically rough surface | Turquoise |
| Pearly | Overlapping parallel lamellae | Moonstone |
| Silky | Finely fibrous structure | Gypsum |
| Metallic | The brilliant appearance of metal. | Gold, pyrites |

Sheen is due to reflection of light from below the surface of the coloured gemstone. It is caused by the internal structure of the gemstone and there are several distinctive types, as described in the following Table:

| Sheen | Description | Example |
| --- | --- | --- |
| Iridescence | Rainbow effect often observed in cracks and flaws in a stone | Quartz, calcite, iris agate, labradorite, orient of pearl |
| Labradorescence | Diffraction at alternating layers | Spectrolite, labradorite |

-continued

| Sheen | Description | Example |
| --- | --- | --- |
| Adularescence | Sheen of silvery light crossing the gemstone caused by alternating layers of different feldspars | moonstone |
| Opalescence | Scattering of light from small particles in the stone, milky translucent effect | Common opal/ opal glass |
| Play of Colour | Used to describe the colours seen in precious opal | Opal |
| Chatoyancy | Reflection effect due to parallel fibres, tubes or needles of included substances on a cabochon cut stone | Quartz, tigers-eye, chrysoberyl |
| Asterism | Mobile star effect from parallel fibrous inclusions aligned with specific crystal directions | Ruby, sapphire, almandine garnet, chrysoberyl, diopside |
| Aventurescence | Specular reflections or spangles of light reflected from plate like inclusions | Aventurine quartz, sunstone |

Inclusions which interfere with the transfer of light through the coloured gemstone may reduce its value, whilst other inclusions prove its authenticity, yet other inclusions provide a welcome effect such as the layered rutile needles present in star sapphire and ruby which if present, cause a pleasing star effect to appear on a cabochon cut corundum (sapphire and ruby) or the chatoyancy of cats eye chrysoberyl.

Traditionally, colour grading at gemological laboratories is carried out by the human eye. For instance, when colour grading a diamond, a gemologist will line up a master-set of diamonds (featuring a D to Z colour) to which the diamond's colour is compared. The master-set of stones and the diamond are placed on a dull white countertop. The master-set is lined up with lightest (the top colour) first, becoming progressively darker. The diamond's colour is then compared to the colour of each stone of the master-set until the grader perceives its colour to be the same.

Several problems arise when a human observer grades a diamond: every eye has a different "colour deficiency". This means that every grader has deficiencies for certain colours. Further, the colour and intensity of illumination influences the eye's perception. This results in deviations in colour grading of large diamonds (a few carats) and small diamonds (a few tens of points) as most master-sets feature diamonds of around one carat in size. Finally, larger labs will use two different master-sets with inevitably slightly different colours. As such, colour grading within the same lab or between its branches may vary.

There have been numerous attempts to provide standardised reporting systems for the colour grading of gemstones. One prominent system is provided by the Gemological Institute of America (GIA). Its report provides detailed information about the dimensions, carat weight, shape and cut of a gemstone. GIA reports also cover any treatments or enhancements that have been done and of course, whether the stone is natural or synthetic. A GIA report utilizes a standardised "coloured stone grading system" chart to graph the hue, tone, and saturation of a stone. Gemstone colour grading is broken into three quantifiable categories: intensity (saturation), hue (colour), and tone (lightness/darkness).

The GIA specifies and labels up to thirty one gemstone hues according to the gemstone hue chart. The "hue" is the actual "colour" of the material (blue, green, red, etc.).

The GIA nomenclature also specifies six levels of saturation ranging from "grayish" (neutral grey) to "moderately strong" to "vivid" according to a gemstone saturation chart. The term "intensity" is also used to describe a stone's saturation.

To describe the darkness or lightness of a coloured stone, the GIA system has nine levels of tone ranging from "very very light" to "very very dark" according to a gemstone tone chart. A numerical value is assigned to each label for use in a grading report.

With the exception of hue, each of these parameters by themselves are relatively meaningless and they must be used together to meaningfully reveal a gemstone's colour quality. Taken together, these three parameters will provide a simple numeric code that can quickly and accurately quantify gemstone colour.

Reports are also provided by the American Gem Trade Association and by American Gemological Laboratories. All of these reporting systems, however, use different criteria and standards of colour grading and so can be confusing when considered together.

Alongside colour quality as a criteria for grading gemstones, brilliancy is the amount of flash the gem returns to your eyes. Most diamonds are 100% brilliant. An average brilliancy of 50% means half of the stone returns flash.

The Gëbelin Gem Laboratory in Lucerne, Switzerland (GGL) is one of the leading testing laboratories in Europe, testing coloured stones, fancy coloured diamonds, colourless diamonds, and pearls. They also test diamonds for any sign of (HTHP) enhancement. Coloured stones are tested for the usual parameters of clarity, colour, cut, and enhancements as well as place of origin, Diamonds are tested for clarity, colour, fluorescence, cut, and symmetry.

Generally, the grading criteria for coloured gemstones, in order of decreasing importance, can be summarised as comprising the following:
Colour
   Hue
   Saturation
   Brightness
Cut
   Shape
   Proportion
   Symmetry
Clarity
   Inclusions mapped
   Verification of type as pertaining to gemstone variety
   Degree of transparency of the gemstone
Carat Weight
   As per industry standard
Scintillation
   Surface reflection/refraction from smaller facets—"twinkling" effect as the stone is moved
Brilliance
   Return of light from the gemstone which has been internally reflected and hence has colour produced by filtering through the coloured material of the gemstone
Lustre
   Surface feature of the gemstone—analogous to the fineness of polish; high lustre produces sharp edged surface reflections while low lustre produces dull or fuzzy edged surface reflections
Dispersion
   Resulting from the breaking up of white light into its spectral components—more characteristic of diamonds than other coloured gemstones, coloured gems show low dispersion
Sheen
   Play of light due to the internal characteristics of the stone

DISCLOSURE OF INVENTION

It is an object of the present invention to overcome or substantially ameliorate the aforementioned shortcomings and problems of the prior art, or to at least provide a useful alternative.

It is another object of the present invention to provide apparatus and methods for assessment, evaluation and grading of gemstones in an objective, consistent and automated manner so as to allow standardisation of opal and other gemstone quality analysis and grades, thereby improving the confidence to trade of the sellers and also the buyers and adding certainty to the prices they may be prepared to accept or pay for a gemstone.

The disclosure in International Patent Application No. PCT/AU2008/000459 is incorporated herein by reference. The apparatus and methods disclosed therein may, to the extent that would be readily appreciated by a person skilled in the art, be useful for the purposes of the present invention. This applies to both the hardware and software, and particularly to colour calibration and segmentation and histogram analysis.

According to the invention, there is provided an apparatus for assessment, evaluation and grading of gemstones, comprising a stage upon which a gemstone may be supported, the stage being enclosed in a housing that is impervious to light, at least one light source located in the housing and adapted to project incident light onto the gemstone, means for rotating and tilting the stage so as to vary the orientation of the gemstone to the incident light, a digital camera located in the housing adjacent the or each light source and adapted to take images of the gemstone based on reflection and/or refraction of the incident light, and information processing means for calibrating and analysing the images, wherein the information processing means is programmed with instruction sets for assessing one or more of colour, cut, clarity, scintillation, brilliance, lustre, dispersion and sheen, and wherein the gemstone is supported upon the stage by securing means engaging the gemstone at its bottom surface.

It is preferred that the stage is rotatable around 360° and tiltable around 90°, and may be part of a goniometer.

It is important that the camera and the or each light source be positioned as close as possible together so as to mimic human opal grading, wherein the or each light source is as near co-incident as possible to the camera axis.

Preferably, colour assessment of the gemstone is with an instruction set for colour calibrating the images and then analysing the colour calibrated images by segmentation and histogram measurement.

BRIEF DESCRIPTION OF THE DRAWINGS

FIG. 9 is a 2D histogram summarizing the gemmological characteristic of a gemstone derived from the use of the apparatus (including software) of FIGS. 1 to 6.

MODES FOR CARRYING OUT THE INVENTION

Figure 1:
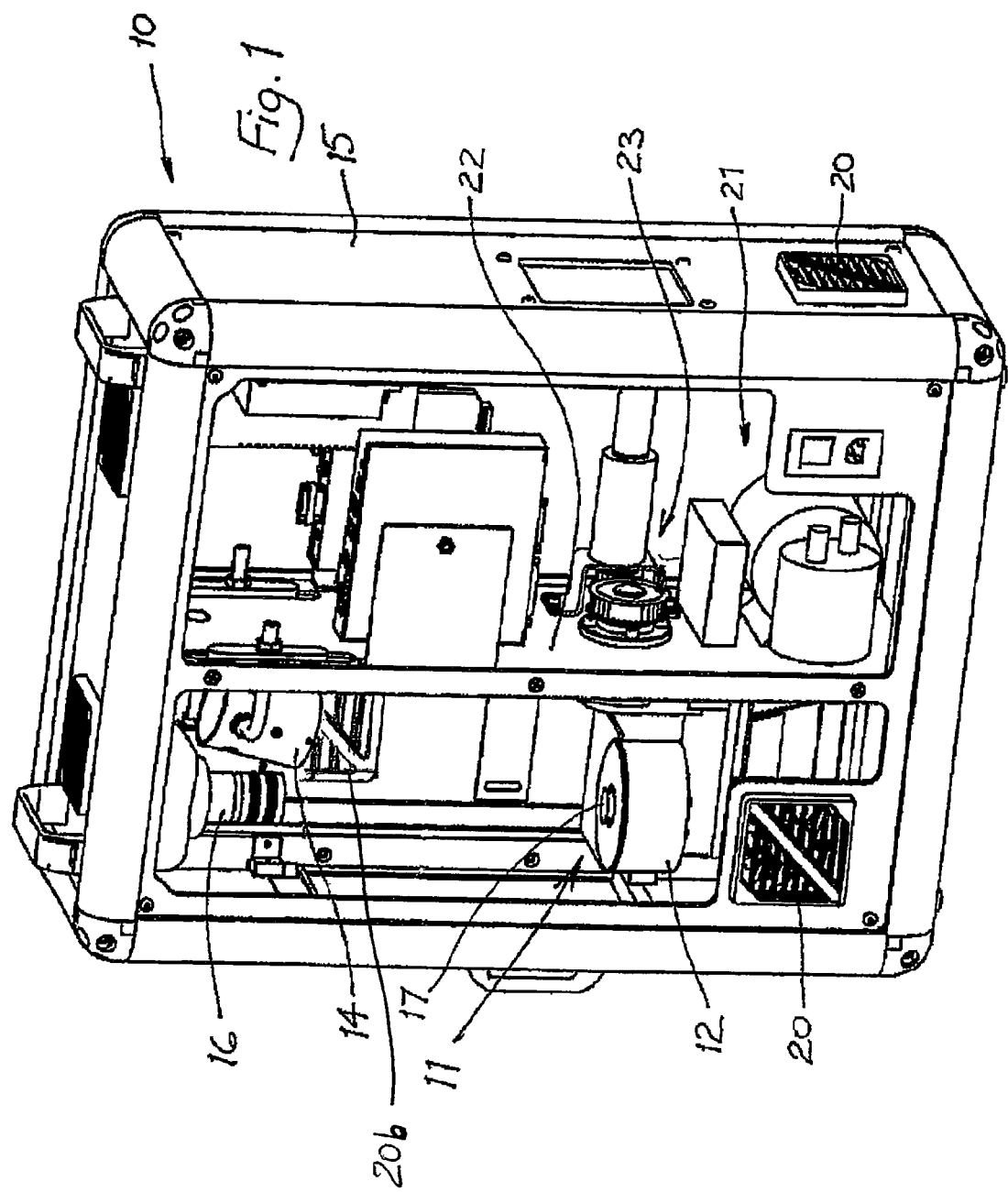
FIG. 1 is an isometric side view of a gemstone assessment, evaluation and grading apparatus according to a first embodiment of the invention.
Figure 2:
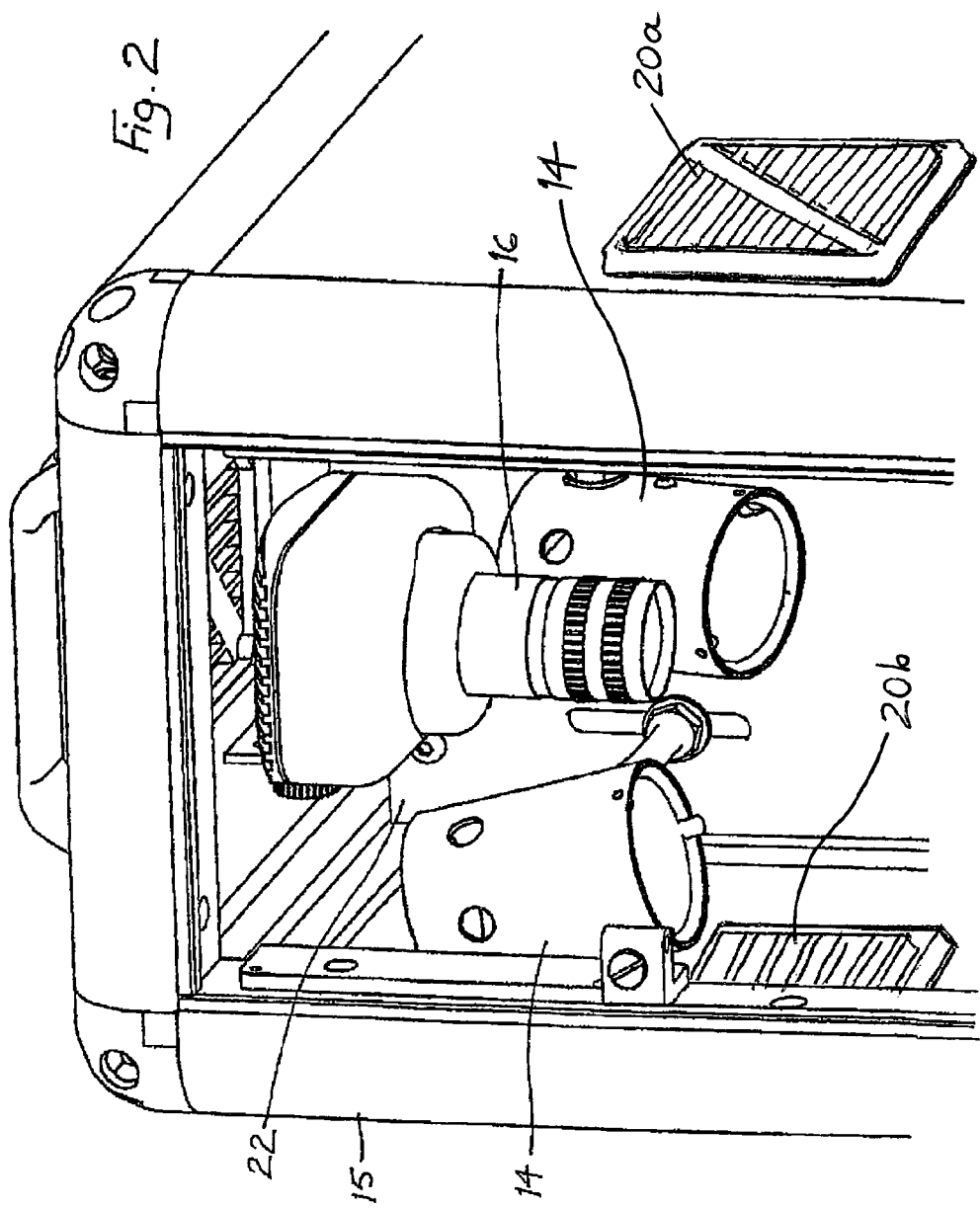
FIG. 2 is a view of the camera and lighting arrangements of the apparatus of FIG. 1.
Figure 3:
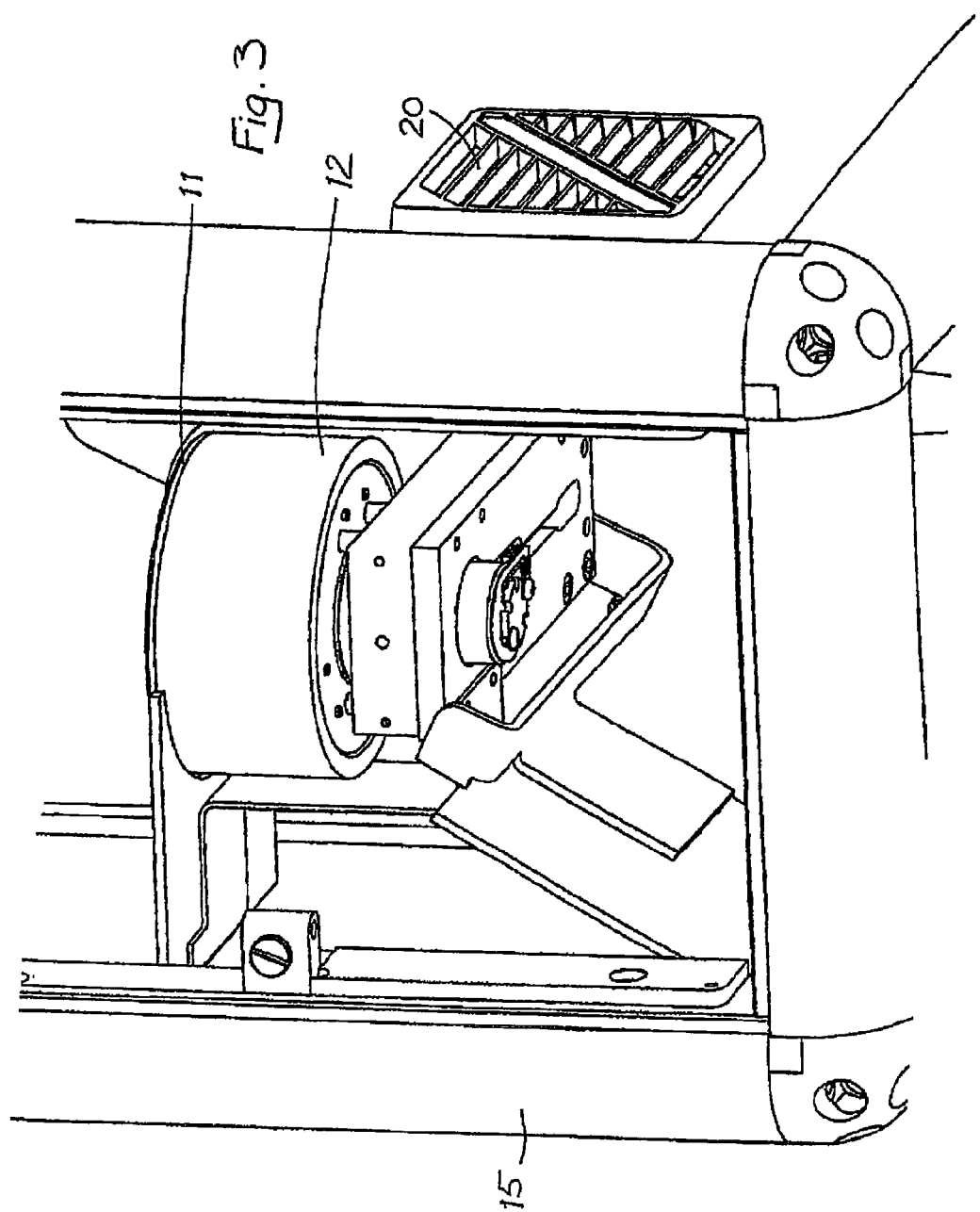
FIG. 3 is a view of the rotatable and tiltable stage arrangement of the apparatus of FIG. 1.
Figure 6:
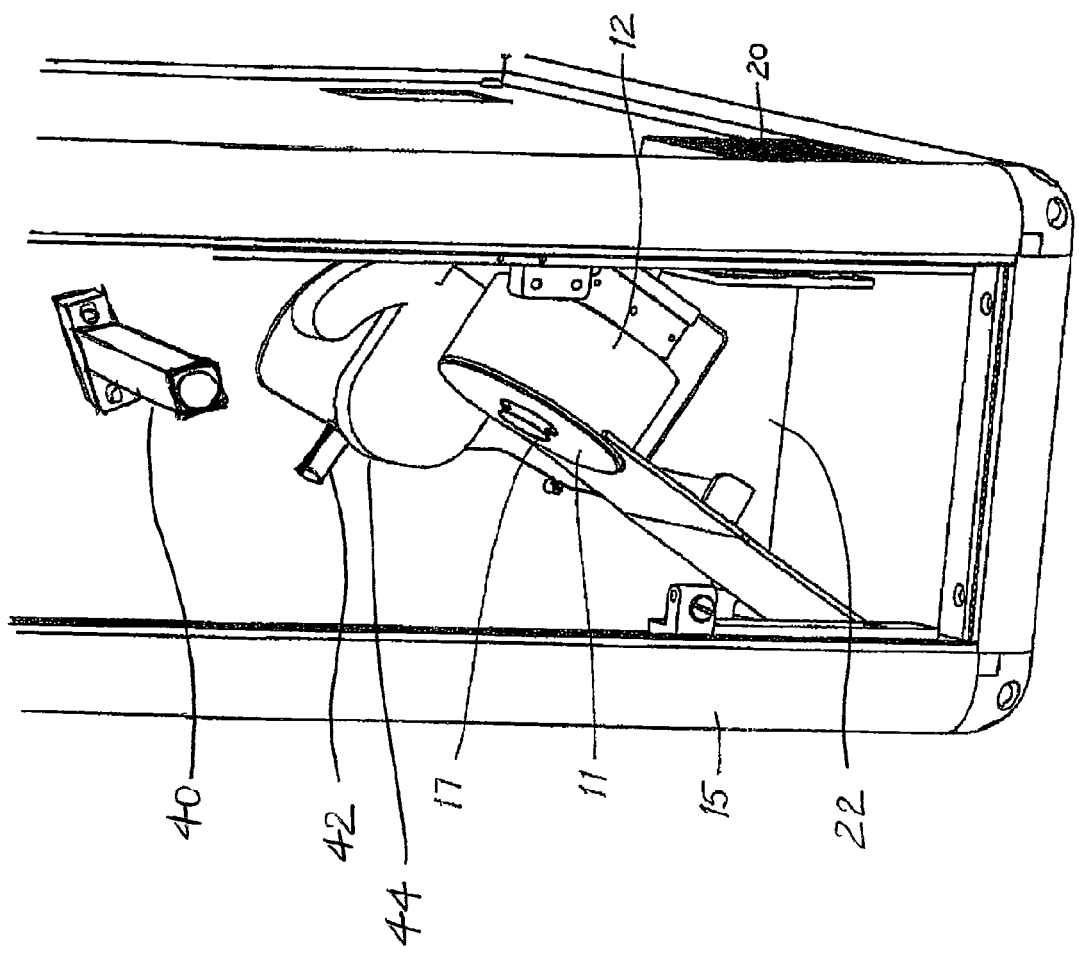
FIG. 6 is a view of the stage arrangement shown in FIG. 3 in a tilted position.

Referring to the apparatus 10 shown in FIG. 1, an opal is able to be placed on the stage 11 or platform of a goniometer 12, with the stage 11 being tiltable and rotatable by movement of the goniometer as shown in FIG. 6. The opal may have a maximum size of 5×5×2 cm for the stage 11. In this specification, the tilt and rotation angles will be referred to by the symbols $\phi$ and $\theta$, respectively. A level or horizontal position of the stage corresponds to a reading of $\phi=90°$ when a calibrated electronic digital camera 16 and one or more calibrated artificial light sources 14 (see FIG. 2) are directly overhead. From the level position, tilting the stage 11 away from the one or more light sources 14 resulted in a reading decreasing from $\phi=90°$ to $0°$.

Figure 4:
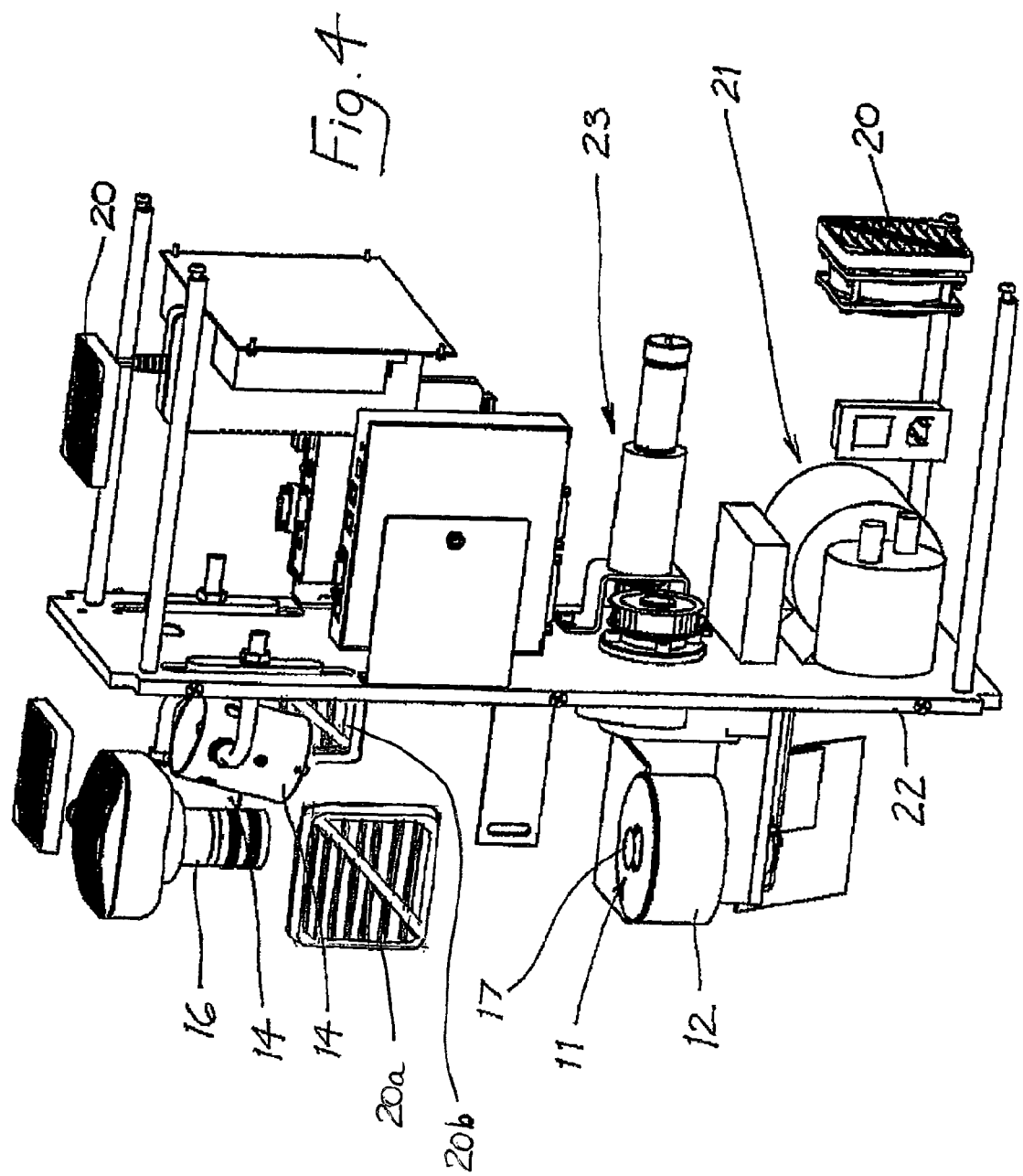
FIG. 4 is a view of the apparatus of FIG. 1 with its housing removed to show internal features.
Figure 5:
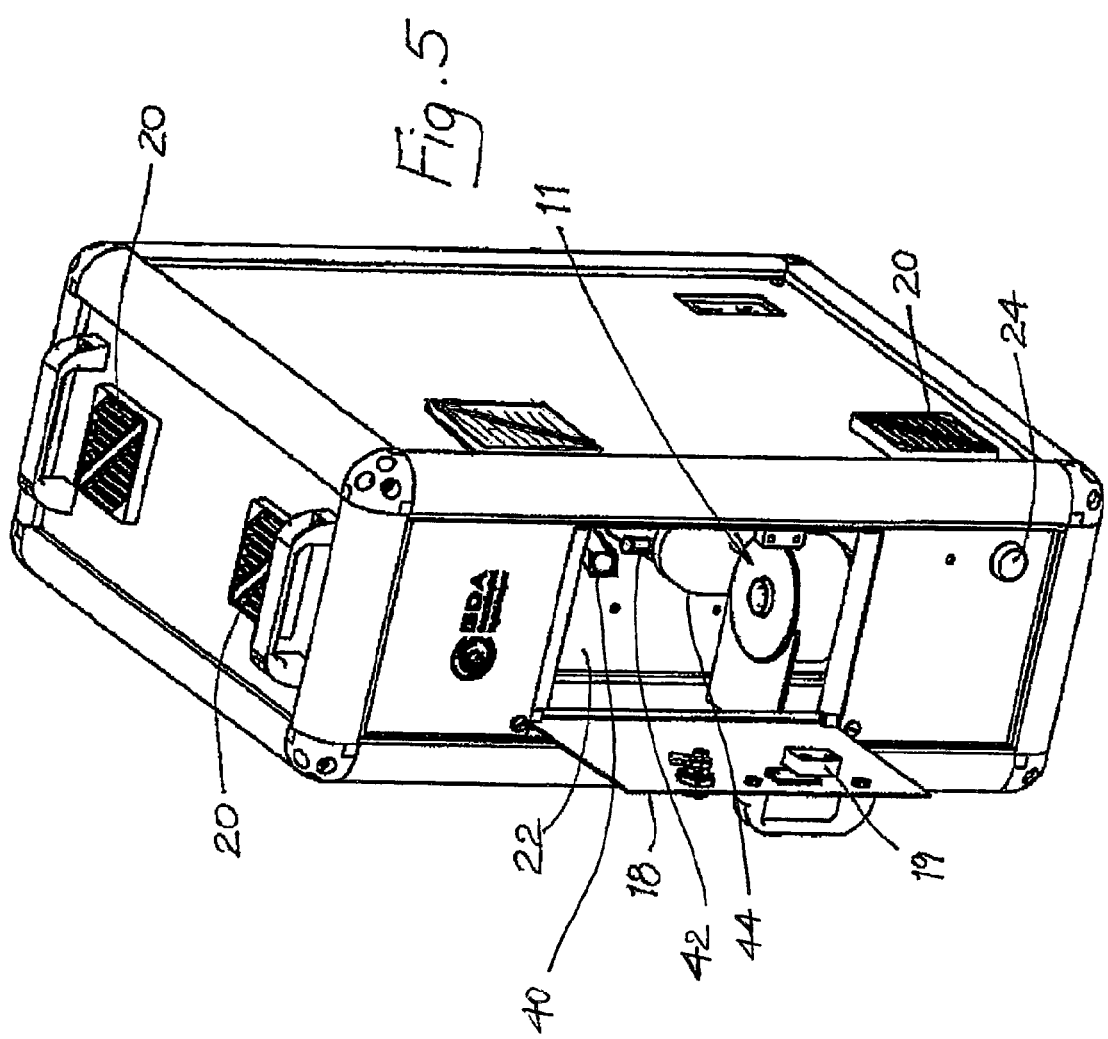
FIG. 5 is a isometric view of the apparatus of FIG. 1 with the door of the housing open.

The apparatus includes a light impervious housing 15, and the relative positions of the camera 16, the light sources 14 and the goniometer 12 within the housing are shown in FIG. 4. The position of the light sources 14, which are rotatably mounted, is alongside the camera 16, such that they are equidistant from the stage and the light sources 14 are as near co-incident as possible to the camera axis (i.e. over the shoulder). This is to replicate the lighting conditions used for human opal grading.

The housing 15 has an access door 18 for loading the opal onto the centre of the stage 11. The door 18 has a solenoid lock 19 so that it can be opened only when safe to do so, such as when the stage 11 has ceased any movement. When opened, the stage 11 will not be able to move.

Light proof, cooling fans with vents 20 are provided at the top and lower sides of the housing 15 to allow for convection cooling of the apparatus. On opposite sides of the light sources 14 and the camera 16 are a cooling fan with vent 20a and a vent grille 20b.

There is a motor control unit 21 located within a section of the housing 15 that is separated by a wall 22 from the camera 16, light sources 14 and the goniometer 12. The unit 21 has an on/off switch 24 and indicator lamp, and includes servomotor driver cards, contactors of lamps, safety circuitry and a main isolator connected to a personal computer (not shown) at which image calibration and image analysis will be controlled by software. A shaft and gearing assembly 23 driven by the motor control unit 21 controls the rotation and tilting of the goniometer 12 and its stage 11 in cooperation with a movement limit switch assembly. There is a homing inductive sensor or switch 40 mounted to wall 22 and a homing metal spigot 42 mounted to a crank arm 44 of the motor control unit 21. The limit switch assembly is positioned so as to safely control or preset the limits in the range of movement of the stage 11.

In order to quantify the colour characteristics of an opal, the two characteristics of flash or "play of colour" and body tone are critical.

The camera 16, which is automatically synchronized with the movement of the stage, captures a series of images at multiple angles in order to quantify the flash over the full range of viewing angles. Several image capture geometries are possible, such as tilting the rotation stage 11 holding the opal while keeping the camera and light sources fixed, or moving the camera and light sources while keeping the tilt angle of the rotation stage fixed, or some combination of these.

Initially the camera 16 is positioned directly above the rotation stage 11 containing the opal, wherein the stage is positioned at a tilt angle of 90°.

With back lighting, one image is captured to determine if the opal is translucent (i.e. crystal) and also to determine the region of interest (ROI) within the image that contains the opal.

With forward lighting, thirty-six images are captured at 10° intervals for 0° to 360° of rotation, although 5° intervals may be better suited to some opals. This series of images is repeated for 10° steps of tilt angle of the stage until a side view of the opal is achieved. Some opals may be better suited to 5° intervals of tilt angle. Although not shown, the camera 16, rather than the stage 11, may be adapted to tilt.

The opal is held tightly to the stage 11 by a flexible, silicon based suction cup 17 using suction from beneath the opal. By making the suction cup and the tubing from the suction cup to the vacuum pump of translucent material, this system does not occlude the opal in either forward or back lit views. It is capable of holding the opal firmly enough that the stage 11 can be tilted from 90° (overhead view) to 0° (side view) without the opal falling off. This means that a user or developer of the apparatus can choose the implementation which uses stage tilt rather than camera movement. This has the advantage of having a smaller footprint than the implementation that moves the camera.

Software is used to analyse these images to extract a summary of the flash and body tone characteristics and to display these measures in an easily comprehended manner. A description of each step in the software controlled analysis is provided later in the specification.

It will be apparent that the apparatus and methods described herein can be readily adapted for assessment, evaluation and grading of all coloured gemstones (including diamond, sapphire, ruby, and emerald).

Colour images were acquired using the camera 16 (Micropublisher RTV 5.0 manufactured by Qimaging). This camera has a dynamic range of 10 bits, corresponding to 1024 pixel intensity levels for each red, green and blue (RGB) channel (corresponding to a total of roughly one billion colours that the camera can discriminate). The number of pixels is 2560× 1920. The lens attached to the camera was a Randd Electronics macro lens. The focal length was 25 mm and the aperture was set to f/8.

As a light source 14, an incandescent light bulb was used. The glowing filament of an incandescent light bulb produces light with a broad spectrum. So, in terms of the breadth of its spectrum, it is more similar to daylight than other light sources, such as fluorescent tubes or light emitting diodes (LEDs) which have narrow spikes in their spectral distribution. The potential exists for the application of a light source in a "diffused" manner or oblique manner, so as to remove glint.

Seen from the position of the opal, the light bulb is a directional light source, covering an angle of approximately 9.1°. A disadvantage of directional illumination is that specular reflections from the surface of the opal, also called glints, can reflect the bright light of the light bulb directly into the camera. For surface positions where glints occur, the camera sensor is saturated and no information about the colour and brightness of the opal can be obtained. Therefore, areas of glint have to be detected in the images and excluded from further analysis, as described later in the specification.

A simple model for explaining the occurrence of flashes is to assume that facets within the opal act like small coloured mirrors. The viewer (or the camera) will therefore observe a flash when the angle of light incident on the opal is the same as the viewing angle. For a given light source, the observed area of flash will therefore depend on the solid angle covered by the light source. The smaller the solid angle (i.e. the more directional the light source), the smaller the area of flashes. For a large area light source, which is covering a large solid angle, flash will be observed over a larger area of the opal. Note that for the area of flash to become an objective criterion for assessing the quality of an opal, the directionality of the light source will have to be standardised.

For the image acquisition, each opal was placed on the suction cup 17 at the centre of the stage 11 of the goniometer 12 and secured with suction to prevent it from sliding off the stage at large tilt angles.

For all opals, the tilt angle $\phi$ was varied over a range of 90° in steps of 10°.

The rotation angle $\theta$ was also varied from 0° to 360° in steps of 10°.

A controlled switching application of the light sources 14 was used to measure the "play of colour".

As will be described in more detail later in the specification, the images taken at two different exposure times were combined into a single image with extended dynamic range. For this, the image taken at the long exposure time of 32 ms was used as a basis. Pixels that were fully saturated were replaced with the pixels from the image taken at 2 ms.

The extended range images obtained with the camera 16 are not suitable for calculating the colour and brightness values of the opals. First, lighting non-uniformities need to be corrected. Then, because each light source and camera has slightly different characteristics, the device-dependent RGB image needs to be calibrated to a device-independent measurement of colour. This measurement of colour needs to be appropriate for describing the colour characteristics of flash and body tone in terms that a person will understand.

For all types of coloured gemstones, it is necessary to colour calibrate all the images prior to analysing their content. It is also necessary to segment the portion of each image containing the coloured gemstone. These steps for all coloured gemstones will be substantially the same as for opals as described in International Patent Application No. PCT/AU2008/000459 and incorporated herein by reference.

All coloured gemstones have a number of attributes or characteristics that may be measured by these steps. These are as follows:

Attribute Measurements
Colour
   Hue
   Saturation
   Brightness

Unlike opals which display different flash colours at different viewing angles, other coloured gemstones will generally have the same internal colours present when at all viewing angles. We will call it the body colour to distinguish it from the colour due to surface reflections. Most coloured gemstones are not uniformly one colour. They often have two or more body colours present. We can use the histogram binning procedure described in International Patent Application No. PCT/AU2008/000459 to quantify these body colours.

Cut
   Shape

Proportion

Symmetry

For opals, there is no special value or significance associated with the shape of the stone. So there was no automated method for analysing the segmented shape of an opal. For other coloured gemstones, the cut is of considerable significance and tends to be one of several formal shapes, such as antique cushion, baguette, emerald, briolette, pear, marquise, step, trilliant, cabochon and princess.

Consequently there is a need to automatically identify the cut class and to measure the shape parameters specific to that class. To do this we require multiple views of the stone:

- with the stone held at its base, a top view of the stone—showing the shape of the table; from the stone segmentation, the orientation of the best fit ellipse will indicate if the stone is circular or elongated; from this, we can determine the stage rotation angles aligned with the long axis and short axis of the stone,
- with the stone held at its top, two side-on views of the stone at the stage rotation angles of the long and short axes—showing the side profile of the pavilion and the table along the long and short axes.

After segmenting the stone in each of these views, we need to classify the cut. There is a variety of standard shape matching techniques which could be used for this—template matching (using correlation with templates of each class) or classification of rotation and scale invariant shape attributes, such as Zernicke moments or Fourier descriptors (using class rules derived from training data for each class).

Having identified the class of cut, we then need to measure the shape parameters specific to this cut. There are several techniques for this. The simplest method is to custom design parameter measurement procedures for each class of cut. For example, for a baguette cut, the minimum enclosing rectangle of the segmented top view will give the length and width of the girdle. Finding the widest point in the segmented long-axis side view will split the long-axis side profile into the table region and the pavilion region. The length and width of these regions will yield the dimensions and angles of the long-axis of the stone. A similar process on the segmented short-axis side view will give the remainder of the parameters to characterise the baguette cut. The other cuts can be quantified in an analogous manner.

Clarity

Inclusions mapped

Verification of type as pertaining to gemstone variety

Degree of transparency of the gemstone

The transparency of the gemstone can be assessed using the backlit view in the same way that opals are tested if they are crystal. Similarly macroscopic inclusions can be detected by thresholding this image in the same way that crystals are tested for opaque veins of patch. Microscopic inclusions can only be detected in a separate instrument which has the equivalent of a microscope objective to produce ×20 or ×40 magnification of the stone.

Carat Weight

As per industry standard

This is not a feature which can be assessed visually.

Scintillation

Reflection/refraction from smaller facets—"twinkling" effect as the stone is moved.

In opals, the surface reflection called glint is an unwanted phenomenon and is detected solely for the purposes of masking it out when making measurements of body tone or flash. In other coloured gemstones, the surface reflections from the many facets of the gemstone produce scintillation. This can be quantified by measuring the variation in amplitude of glint with changes in rotation angle in the top view of the stone.

Brilliance

Return of light from the gemstone which has been internally reflected and hence has colour produced by filtering through the coloured material of the gemstone Brilliance in other coloured gemstones is analogous to flash in opals. We can quantify brilliance in the same way as we quantify flash in opals.

Lustre

Surface feature of the gemstone—analogous to the fineness of polish; high lustre produces sharp edged surface reflections while low lustre produces dull or fuzzy edged surface reflections This attribute is of most importance for pearls. It can be quantified by reporting the sharpness of the edges of surface reflections, or glint. The method for detecting glint will be the same as that used for opals. This will give a mask of the glint region within the stone mask. The difference between a dilated and eroded version of the glint mask will give a mask of the region containing the glint edge. The amplitude of an edge filter, such as a sobel filter, within this glint edge mask will give a numerical measure of the sharpness of the edge, and hence of the lustre. High edge filter values (sharp edges) will indicate high lustre and low edge filter values (fuzzy edges) will indicate low lustre.

Dispersion

Resulting from the breaking up of white light into its spectral components—more characteristic of diamonds than coloured gemstones, coloured gemstones show low dispersion Dispersion refers to an optical property of gemstones whereby flashes and pinpoints of spectral colours are displayed as the stone is turned in the light. The dispersive colours we see are not really there in the gemstone, instead they are created by the behaviour of white light in the stone. Dispersion results when light passes through a transparent material with inclined surfaces (like a prism or a faceted gemstone). Although the term "fire" is gemmologically equivalent to dispersion, "fire" is so frequently misused to mean either brilliance (total light return) or scintillation (twinkling), that the term "dispersion" will be used in this description for the sake of clarity.

White light is, of course, made up of a spectrum of wavelengths from relatively long (red) to relatively short (blue and violet). Each of these wavelengths is bent to a different degree (red less, blue more) when passing from air into a denser medium like a gemstone. When the bent light waves exit through an inclined surface (like a facet), depending on the degree of bend (or refraction), they may show as distinct spectral colours. The ability of a gem species to show dispersion is, therefore, roughly correlated with the density and refractive index of the gem material itself.

This property is a distinctive characteristic of each gem species and can be used in the process of identifying a gemstone.

Dispersion can be measured with a refractometer and the apparatus of the invention includes such refractometer means. Dispersion is usually expressed numerically as the difference between the red and violet refractive indices.

Sheen or Play of Colour

Play of light due to the internal characteristics of the stone

Sheen in other coloured gemstones is analogous to 'play of colour' in opals. We can quantify sheen in the same way as we quantify 'play of colour' in opals.

"Play of colour" occurs if flash of a specific colour changes position, or if a specific region of flash changes colour, as the viewing angle is changed. Flash histograms will not necessarily detect this as they do not take into account the spatial location of the flash. To measure this attribute, we need to compare images taken with different (say, two) lighting angles for a serious of rotation and tilt angles.

Geometric distortion of the stone will be present if we attempt to compare images from different stage tilt angles. Therefore, it is preferable to compare images taken at different stage rotation angles, or different lighting angles for a 90° stage tilt angle. Images taken at different stage rotation angles must be rotated back in software in order to align them before they can be compared. This step is not necessary if different lighting angles are used. However, if different lighting angles are used, then each separate light source must have its own set of colour calibration files.

A "play of colour" measure must detect both presentations of "play of colour", i.e. change of colour or change of position. There are several ways of doing this. One simple method is to take the average of the absolute difference of the two co-registered views for a series of rotation angles, say every 10 degrees. At a single rotation angle, the "difference" score is defined as the sum of the average absolute difference within the stone mask (but excluding the glint masks) of the two co-registered views for the red, green and blue bands of the sRGB images.

If a flash region changes colour between the two views, then the "difference" score will detect it. Larger colour changes will give a higher "difference" score, as will larger areas of colour change. If a specific flash region moves position but not colour, then the "difference" score will also detect this. The score can be scaled to have a range of 0 to 1 by dividing by the "difference" score of the marker stone with the greatest "play of colour". Alternatively, the score can be scaled from 0 to 100, with scores close to 0 indicating little play of colour and scores close to 100 indicating much play of colour.

Image Calibration
Extended Exposure

The brightness of opals covers a very wide dynamic range, from very dark areas of body tone to flash regions that are typically orders of magnitude brighter. This range of brightness exceeds the dynamic range that a standard camera can capture in a single image. To capture the full range of brightness encountered in opals without losing information due to over- or under-exposure, a pair of images is captured at different exposure times. The chosen camera has a 10-bit dynamic range for each red (R), green (G) and blue (B) channel image giving pixels in the range of 0 to 1023. Images $I_{short}$ and $I_{long}$ are captured at two exposures, 2 ms and 32 ms respectively, and combined to give an image of extended dynamic range, $I_{ext}$, as shown in Eqn 1 below. This gives a brightness range of 0 to >10,000.

$$I_{ext} = I_{long} \text{ if } I_{long} < thr$$

$$I_{short} * \text{exposure.scaling if } I_{long} >= thr \qquad \text{Eqn 1}$$

where thr is 900 and the exposure.scaling is given by the ratio of the means of $I_{long}/I_{short}$ for a standard Kodak White card.

Figure 7:
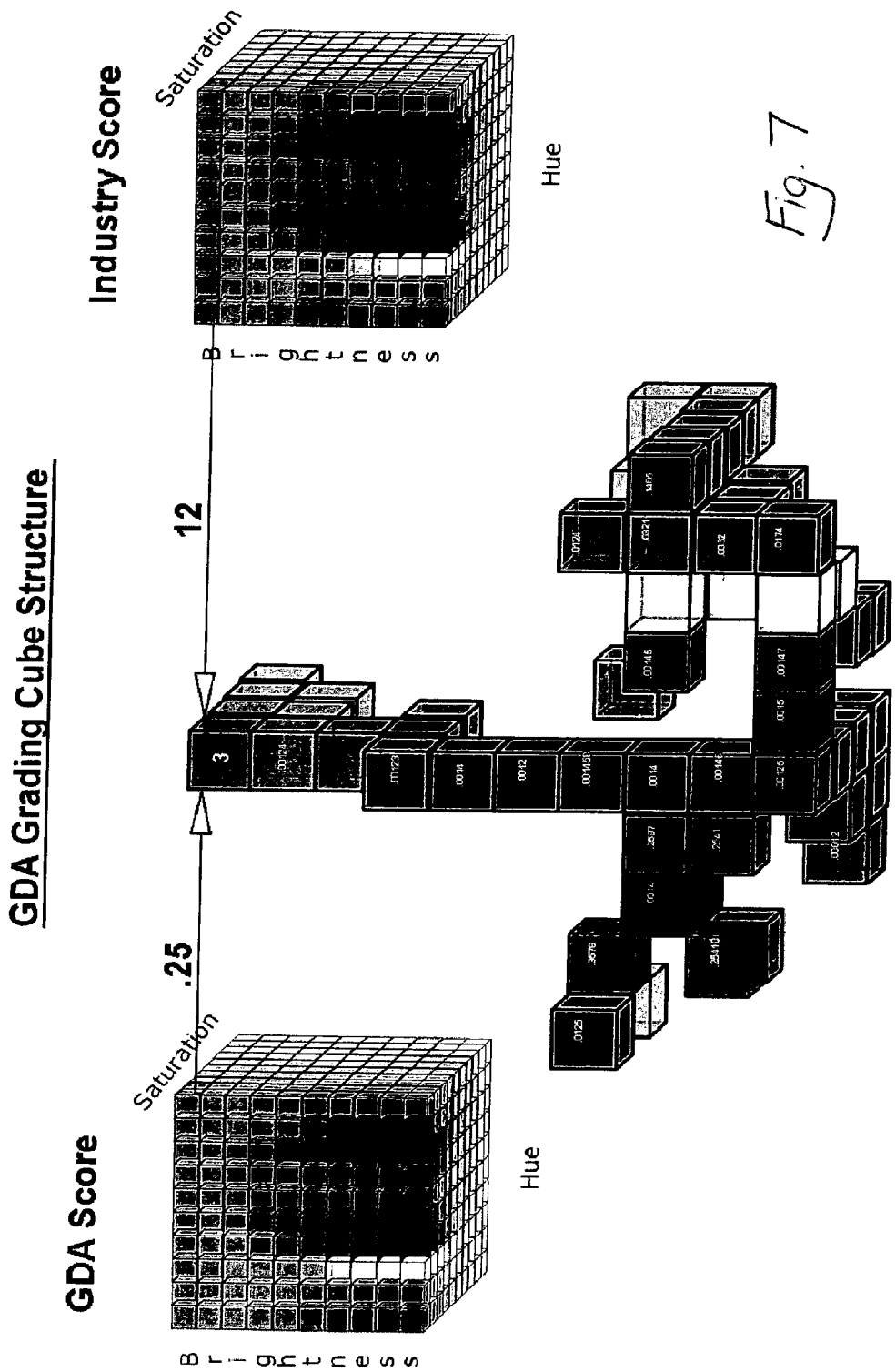
FIG. 7 shows a 3D array cube structure identifying the unique characteristics of a gemstone derived from the use of the apparatus (including software) of FIGS. 1 to 6.

An example is provided in FIG. 7 of herein incorporated International Patent Application No. PCT/AU2008/000459, where there is shown, at left, $I_{long}$ with a horizontal transect taken through the centre of the image showing saturation of the brightest regions of flash (i.e. clipping of the G & R at 1023) and, at right, $I_{ext}$ with the horizontal transect showing that the extended dynamic range removes the saturation of the flash.

Lighting Correction

With a single light source, the lighting is often not uniform across the field of view of the camera. It will tend to be brighter in the centre of the lighting field. To correct for these lighting non-uniformities, two lighting field images are acquired, $I_{white}$ and $I_{grey}$, of standard Kodak White card and Kodak Grey card respectively. The Kodak White card has 90% reflectance across the visible spectrum and the Kodak Grey card has 18% reflectance. Assuming the CCD sensors in the camera are linear, these lighting field images can be used to correct the extended range image $I_{ext}$ consisting of channels $R_{ext}$, $G_{ext}$, and $B_{ext}$. The lighting corrected image $I_{cor}$ is derived as shown in Eqn 2 below.

$$L_{max} = \max(\text{mean}(R_{ext}), \text{mean}(G_{ext}), \text{mean}(B_{ext}))$$

$$I_{cor} = (I_{ext} - I_{grey}) * L_{max} * (90-18)/90/(I_{white} - I_{grey}) + L_{max} * 18/90 \qquad \text{Eqn 2}$$

where $L_{max}$ is the scalar maximum of the means of the channel images.

Colour Calibration

Because the CCD sensors in colour cameras can have different sensitivities and because the spectral characteristics of the light source can up of the apparatus. In other words, it is a device-dependent, relative measure of colour. The process of converting the image to a device-independent, absolute measure of colour is called colour calibration.

Device-Specific RGB to Device-Independent XYZ

In order to convert from device-specific RGB values to device-independent XYZ values as defined by the CIE (Commission Internationale de I'Eclairage, or International Commission on Illumination), we need a calibrated colour checker card such as a Munsell or Macbeth card which has several colour swatches of known device-independent XYZ values. By capturing an image of this card and extracting the mean RGB values for each colour swatch, the transformation matrix, RGB2XYZ, can be determined by linear regression between the measured RGB values and the supplied XYZ values. Thus the RGB values in the $I_{cor}$ image can be converted to XYZ values in the $I_{XYZ}$ image using this matrix.

Device-Independent XYZ to Gamma'd Device-Independent sRGB

Although the device-independent XYZ measure of colour is an internationally recognised standard for colour representation, it is linear (unlike the human visual system) and not easily understood by non-experts, so it has been converted to a standard RGB representation, called sRGB. The D65 illuminant of this standard is designed to match noon daylight which is typical of home and office viewing conditions. The non-linear transfer function (gamma curve) closely matches that of the human visual system. If sRGB images of opals are viewed on sRGB calibrated monitors, they will closely match the actual opal appearance if viewed under natural daylight (D65 lighting conditions). So the $I_{xyz}$ image is converted to the sRGB calibrated image, $I_{sRGB}$, using the standard transformation matrix, XYZ2sRGB, shown in Eqn 3 below.

$$XYZ2sRGB = \begin{array}{c} R \\ G \\ B \end{array} \begin{pmatrix} X & Y & Z \\ 3.240479 & -1.537150 & -0.498535 \\ -0.969256 & 1.875992 & 0.041556 \\ 0.055648 & -0.204043 & 1.057311 \end{pmatrix} \qquad \text{Eqn 3}$$

Gamma'd sRGB to Non-Linear Look-Up Table'd sRGBlut

The sRGB standard is designed for display of images of diffuse reflecting objects such as the body tone of the opal.

Figure 8:
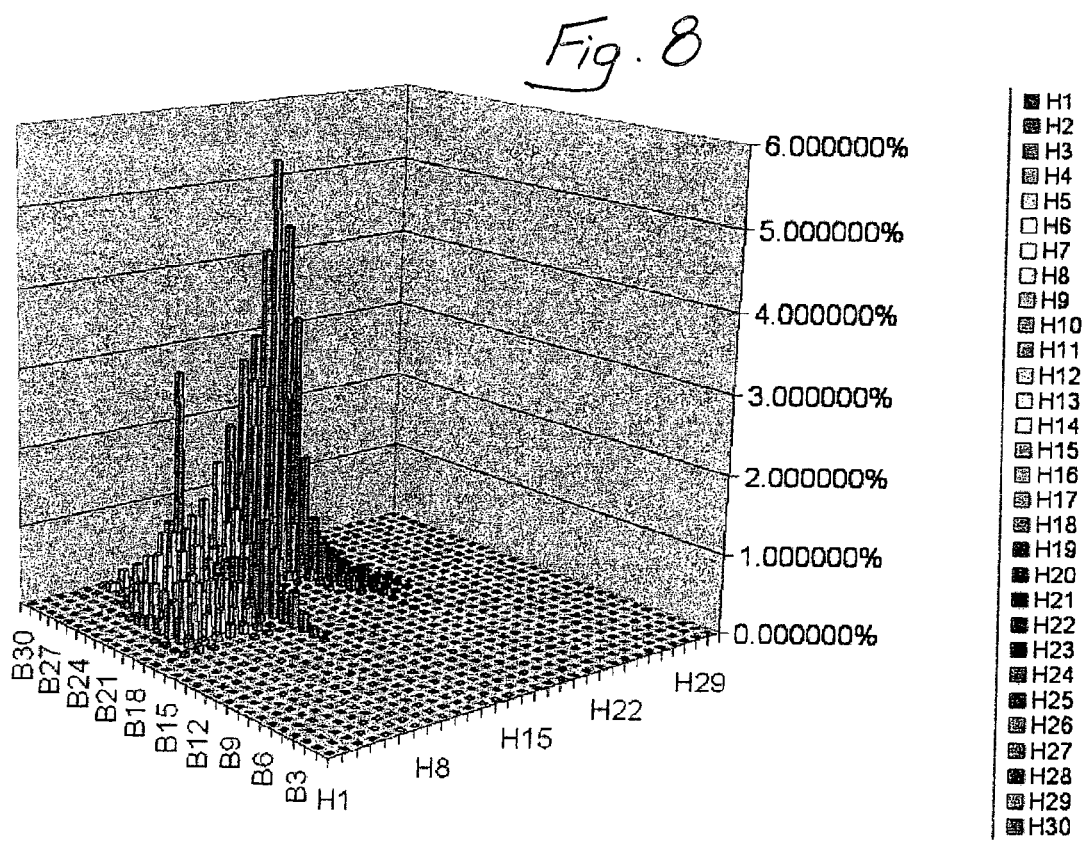
FIG. 8 is a 3D graphical representation of the colours present in a gemstone derived from use of the apparatus (including software) of FIGS. 1 to 6.

Because the flash is specular reflection from the internal crystal structure of the opal, it can be orders of magnitude brighter. No single image display will be able to accurately represent the colour of both the body tone and the flash. For this reason, a Look-Up Table (LUT) has been used to compress the dynamic range of the flash so that a realistic view of the body tone can co-exist with an approximate representation of the flash. This LUT is designed to be linear in the brightness range of the body tone, 0-Bflash (where Bflash ~700) and to compress flash brightness >Bflash as shown in FIG. 8 of herein incorporated International Patent Application No. PCT/AU2008/000459. Applying this LUT to IsRGB gives the image $I_{sRGBlut}$, as shown in FIG. 9 of herein incorporated international Patent Application No. PCT/AU2008/000459, where there is shown, at left, $I_{sRGB}$ indicating the true colour of the bright flashes but the body tone is relatively dark and, at right, $I_{sRGBlut}$ giving a true representation of body tone colour but the bright orange flash regions appear more yellow because of saturation.

Colour Transformation from sRGB to sHSB

The RGB representation of colour is commonly used in image capture and display devices, but it is not designed for describing human perceptions of colour. For this, transformation to an alternative representation of colour called HSB (or HSV) is required. HSB stands for Hue, Saturation and Brightness (also known as Value). Hue is a measure of the wavelength of a colour and is given as an angle between 0 and 360°. Saturation is a measure of the purity of colour or the amount of white added. A pure colour will have 100% saturation. For decreasing values of saturation, the pure colour is increasingly diluted with white. The Brightness (or Value) is a measure of the intensity of the colour. The brightest colour will have 100% brightness. For decreasing values of brightness, the pure colour is increasingly diluted with black. In the extended exposure images provided herein, the brightest colour Bmax (100%) has been scaled to 3000.

Because HSB is a simple transformation of the RGB values in an image, it is defined relative to the standards of the RGB values. Transforming sRGB values will give standardised "sHSB" values, relative to the D65 white point. Applying the RGB2HSB transformation (defined in Eqn 4 below) to the $I_{sRGB}$ image, gives the image $I_{sHSB}$.

$H=0$ if max=min $60°×(g-b)/(\text{max}-\text{min})+0°$ if max=$r$ & $g>=b$ $60°×(g-b)/(\text{max}-\text{min})+360°$ if max=$r$ & $g<b$ $60°×(b-r)/(\text{max}-\text{min})+120°$ if max=$g$ $60°×(r-g)/(\text{max}-\text{min})+240°$ if max=$b$ $S=0$ if max=0

$1-\text{min}/\text{max}$ otherwise $B=\text{max}*B\text{max}$   Eqn 4 where r, g, b are the R, G, and B values, respectively, of a pixel scaled to the range from 0-1; max is the maximum of r, g, and b, and min is the minimum.

Image Analysis by Segmentation and Histogram Measurement

Having colour calibrated all the images captured at the multiple viewing angles, it is necessary to identify the portion of each image containing specific regions of interest, such as the stone or glint. This process is called segmentation.

Segmentation

Stone Segmentation in Back Lit Images

In order to reduce the amount of time taken to capture the multiple images with forward lighting, it is useful to locate the region of interest, ROI, within the image that contains the opal. This is most easily derived from a back lit image rather than a forward lit image because the back lit image has greater contrast between the background and the stone. Therefore the first image to be captured is a back lit view with the stage tilt angle at 90°. This is easily segmented by simple thresholding of the average brightness of the three channels as shown in FIG. 10 of herein incorporated International Patent Application No. PCT/AU2008/000459. The ROI so derived can be used to restrict the area of the image to be captured and processed for all the forward lit images. This can greatly reduce the time to measure each opal.

In the case of translucent, crystal opals, an additional threshold is used to locate any opaque veins of potch running through the crystal. A mask of these opaque regions is required later when determining the body tone of the stone.

Stone Segmentation of Forward Lit Images

Unlike the back lit image, segmenting the forward lit images is a much more challenging task for several reasons. The opal can be both brighter than the background (in the case of white opals) and darker than the background (in the case of black opals). Also, depending on the angle of tilt of the stage, the brightness of the background varies in intensity from nearly white (when viewed from the top) to nearly black (in the side-on view). So a simple threshold cannot be used to separate the opal from the background. In addition, shadows at the edge of the opal mean that simple measures of the uniformity of colour and brightness of the background cannot be used to segment the opal.

The segmentation is performed on the LUT-compressed $I_{sRGBlut}$ image (see FIG. 11 of herein incorporated International Patent Application No. PCT/AU2008/000459) since it gives more weight to the part of the dynamic range containing the transition between background and stone. The segmentation algorithm is a sequence of operations, roughly as follows: transform the image into a form that enhances non-uniformities such as the edges of the opal, colour texture and the edges of flash (the transform used is the maximum of the local pixel-wise variance of the R, G and B channels); threshold this image to get seeds within the opal (high variance); generate background seeds that are an empirically determined distance from the opal seeds; and find the watershed boundary between the two sets of seeds in the gradient of the variance image.

Glint Segmentation of Forward Lit Images

Having defined the mask of the opal, the portion of the opal containing glint needs to be excluded. This is easily segmented by using the fact that glint is both bright (high Brightness or Value) and white (low Saturation). It is simplest to take the logical AND of the results of thresholding S<Sglint (40%) and B>Bglint (1200) of the $I_{sHSB}$ image (see FIG. 12 of herein incorporated International Patent Application No. PCT/AU2008/000459).

Body Tone Segmentation of Forward Lit Images

As described above, the mask or ROI of the image containing only the opal has been determined by excluding the glint regions and, in the case of crystal opals, by excluding the internal opaque regions since these will interfere with the measurement of the body tone of the crystal. Now the regions which display body tone need to be determined before the colour characteristics of that body tone can be measured. If the stone only has opal in its face, then the body tone regions will be those where the flash is "turned off", in other words, where it is not visible from that viewing angle. These regions will be the darkest part of the stone. However, this simple definition of body tone region is not valid in all cases. If the stone has either potch (opal without the crystal structure which causes flash) or boulder (the rock in which the opal is embedded) present in the face, then the darkest part of the stone may well belong to these "non-opal" regions rather than to the body tone of the opal present in the face.

To distinguish between opal and "non-opal" regions of the stone, use is made of the fact that "non-opal" regions remain the same when viewed from different angles. Geometric distortion of the stone will be present if a comparison is made of images from a stage tilt angle other than 90°. This means that a comparison must be made of images taken at different stage rotation angles (or different lighting angles) for a 90° stage tilt angle. Images taken at different stage rotation angles must be rotated back in software in order to align them before they can be compared. This step is not necessary if different lighting angles are used. If different lighting angles are used, then each separate light source must have its own set of colour calibration files. The "non-opal" regions are those which do not change their appearance in these multiple view images.

Flash Histogram Measurement

Unlike body tone which is view-angle independent, the flash in an opal changes from each viewing angle. In the hardware set-up of the apparatus, it has been established that a sampling frequency of 10° is necessary in both rotation and tilt angles to ensure that no flash regions are missed. This requires the capture and analysis of 648 images to cover the full range of viewing angles and full range of brightness encountered in opals. This is challenging to measure and even more so to display in a way which conveys a summary of these measurements.

3D Histogram of Stone HSB Values

For each image, a stone mask has been identified which excludes the background and glint regions. No attempt has been made to exclude "non-opal" regions or body tone regions because these are only established at one tilt angle. A summary of the stone colour characteristics is created by taking a histogram of sHSB values present within the mask. Each histogram is a 3D array of the counts of pixels falling within bins of Hue, Saturation and Brightness value. There are 30 Hue bins linearly spaced in the range of 0 to 360°. Saturation has 10 bins between 0 and 100%. Brightness has 30 bins piece-wise linearly spaced to give 10 bins in the range containing body tone (0-Bflash) and 30 bins in the range containing flash (Bflash-Bmax).

If the pixel count in each bin is divided by the number of pixels in the stone (including glint regions), then the bin value gives the proportion of the stone having the HSB values of that bin.

This is a very compact summary of the colour information. For example, the opal image may be 800×800 pixels. This requires 640,000 HSB values to store and display the colour information. By discarding the spatial context, the 3D histogram requires only 9,000 bins (30 H bins×10 S bins×30 B bins) to store this information. Also, because the spatial context has been discarded, histograms from multiple views can be added to get the average proportions of the stone having specific HSB values.

Put another way, the pixel count (or area) of each colour is exported into one of 9,000 bins. The 9,000 bins are representative of 30 colours (hues), 30 brightness and 10 saturation levels, for the various areas of flash present in opals. The relative area, or pixel count of each colour, is presented as a percentage of the total area of the opal and the data for each specific bin is calculated and reported in the respective bin.

The summary 3D stone histogram (also referred to as a total or full 3D histogram, see FIG. 15 of herein incorporated International Patent Application No. PCT/AU2008/000459) contains bin counts for both flash and body tone regions of the stone. These can be separated out by using the knowledge that flash is both bright B>Bflash (700) and quite highly saturated S>Sflash (50%). (Note that these flash Brightness and Saturation thresholds may be lowered if the Saturation values of the body tone and "non-opal" regions are known). The result is a 3D histogram of flash HSB values.

Summary Histograms of Flash H & B and H & S Values

The 3D flash histogram can be stored but it is difficult to display for easy human interpretation. Consequently, all the Saturation bins are first combined and a 2D summary histogram of Hue and Brightness values is created (a "Summary H&B Histogram"). Also, all the Brightness bins are combined and a 2D summary histogram of Hue and Saturation values is created (a "Summary H&S Histogram").

Summary H&B Histograms and H&S Histograms for two opals, "Golden Grace" and "Flatspot", are shown in FIG. 13 of herein incorporated International Patent Application No. PCT/AU2008/000459.

The H&B Histogram is to be interpreted as follows: Hue is plotted on the x-axis; the height of each histogram bar is the area proportion of that Hue; within each bar, gradations of brightness are used to display the proportions of the area belonging to the various Brightness bins for that Hue. Similarly, the H&S Histogram is to be interpreted as follows: Hue is plotted on the x-axis; the height of each histogram bar is the area proportion of that Hue; within each bar, gradations of saturation are used to display the proportions of the area belonging to the various Saturation bins for that Hue. Note that these gradations are not as informative because flash does not tend to vary in saturation very much.

Note that according to the Summary H&B Histograms in the aforementioned FIG. 13, the maximum area proportion of a single Hue in "Golden Grace" is only about twice that of "Flatspot". However, when the images taken at 80 degree tilt angle are examined, it is obvious where the "Flatspot" stone gets its name. There is a flat spot in its flash when viewed from above. This information is not at all evident in the Summary Histogram. For this reason, 9 additional H&B Histograms were produced to summarise this directional information.

Directional Histograms of Flash H & B Values

The Directional H&B Histograms for "Golden Grace" and "Flatspot" are shown in FIG. 14 of herein incorporated International Patent Application No. PCT/AU2008/000459. Table 1 below defines the range of viewing angles that have been combined for each of the histograms.

The directional histogram for "Flatspot" clearly shows that there is very little flash when viewed from above but it flashes green strongly from the Top Left (TL) direction. By contrast, the directional histogram for "Golden Grace" shows that it displays the largest area of flash and is also most colourful (flashing orange, yellow and green) when viewed from above. This directional information will be important for buyers when choosing an opal for a setting which has specific directionality constraints, such as a pendant or brooch, rather than for a ring which can be easily viewed from many directions.

TABLE 1

Definition of viewing angle ranges for directional histograms where tilt is the stage tilt angle and rot is the stage rotation angle.

| | |
|---|---|
| Above | (tilt > 60°) |
| BC—bottom centre | (tilt <= 60°) & ((rot > 337.5°) \|\| (rot <= 22.5°)) |
| BR—bottom right | (tilt <= 60°) & ((rot > 22.5°) & (rot <= 67.5°)) |
| CR—centre right | (tilt <= 60°) & ((rot > 67.5°) & (rot <= 112.5°)) |
| TR—top right | (tilt <= 60°) & ((rot > 112.5°) & (rot <= 157.5°)) |
| TC—top centre | (tilt <= 60°) & ((rot > 157.5°) & (rot <= 202.5°)) |
| TL—top left | (tilt <= 60°) & ((rot > 202.5°) & (rot <= 247.5°)) |
| CL—centre left | (tilt <= 60°) & ((rot > 247.5°) & (rot <= 292.5°)) |
| BL—bottom left | (tilt <= 60°) & ((rot > 292.5°) & (rot <= 337.5°)) |

The software controlled, image calibration and image analysis method described above is summarised in FIGS. 15a to 15c of herein incorporated international Patent Application No. PCT/AU2008/000459. The image calibration involves the steps of (i) subjecting an opal to extended exposure, (ii) lighting correction, (iii) colour calibration and (iv) colour transformation from sRGB to sHSB. The image analysis involves then subjecting a so calibrated image to (v) segmentation and (vi) histogram measurement, in order to provide an objective assessment of the flash characteristic of the opal. The image analysis may be extended to include body tone measurement.

Body Tone Measurement

In order to measure body tone, 3D histogram bins for the full range of Hue, Saturation and Brightness values within a stone were created in a manner as described earlier in the specification. A method for finding the body tone region in an image, as also described earlier in the specification, involved finding the viewing angle at which body tone was most readily visible. This was a rotation angle displaying minimum flash at 80° stage tilt. Bright flash regions were then excluded, and two regions were classified as body tone and dull flash. The software then calculated the mean or average sRGB values within the darkest 20% of the bodytone region, before converting to HSB values and assigning to one of the 3D histogram bins. The H, S and B value of the body tone can then be reported.

"Play of Colour" Measurement

"Play of colour" occurs if flash of a specific colour changes position, or if a specific region changes colour, as the viewing angle is changed. Flash histograms will not necessarily detect this as they do not take into account the spatial location of the flash. The software compares images taken at two lighting angles for a series of rotation and tilt angles. A method for measuring "play of colour" was described earlier in the specification. "Play of colour" score is the average absolute difference of the two views (excluding glint masks). Scaled from 0 to 100, scores dose to 0 indicate little play of colour and scores close to 100 indicate much play of colour.

Industry Survey

In order to ensure that the results of this apparatus surpassed and were repeatable and consistent with human observers, an extensive industry survey was carried out during the development and testing of the apparatus, which involved the participation from independent and experienced opal industry personnel with cumulative industry experience of over 1,000 years. The participants were asked a series of questions relating to opal assessment, evaluation, grading and valuation, and the results were analysed and incorporated into the design of the apparatus. Participants were also asked to value a series of "marker opals" and other opals of interest that were selected from all opal types and qualities within those types. The industry data was then analysed and averaged, which has then enabled the inventors to construct a series of software algorithms that enable the apparatus to produce results that are consistent and repeatable with comparable grades and valuations.

These same opals were then scanned by the apparatus and the data was computed from the respective opals and the averaged values for the same opals were analysed and aligned to enable the averaged grade values for the 9,000 bins to be established.

In order to establish each opal's "apparatus grade", each opal's 'colour scores' for each cell were multiplied by the respective "grade values" for each corresponding cell, which represents the "apparatus grade" for each of the 9,000 colours (hues), brightness and saturation levels (cells). The individual cell values were then added to give the opal's "apparatus grade" which is unique.

An "apparatus grade" 3D array cube structure showing the unique characteristics or attributes of a gemstone based on a score from the apparatus ("GDA Score") and a score from the industry is shown in FIG. 7.

Valuation of a gemstone is based on a full 3D histogram, but this information needs to be summarised for display purposes. Accordingly, all the saturation bins are combined to create a 2D summary histogram of hue and brightness values. This can be displayed as either a 3D plot (see FIG. 8) where colours present are mapped, quantified and expressed as a percentage related to the area of the stone, or an even more compact 2D plot (see FIG. 9). The latter is useful for displaying directionality effects.

To ensure consistency of results, and particularly the image capture process results, over time, the apparatus is colour calibrated at regular intervals in accordance with procedures conforming to international standards.

Certificate of Authenticity

Use of the apparatus in the manner described above can result in a Certificate of Authenticity which quantifies the individual gemmological characteristics of each opal, such as the colour, body tone, brightness and saturation of all colours present, directionality and other characteristics. These gemmological characteristics are presented in a readable histogram (see FIG. 9) along with the full report of each characteristic in a secure Certificate of Authenticity document.

In summary, it may be appreciated from the above description of preferred embodiments of the invention that:

- High dynamic range imaging (exposure blending) is required to cover the full range of brightnesses between different opals,
- The different brightnesses of an opal can be objectively assessed using a digital camera,
- Under controlled lighting conditions and using proper calibration techniques, the range of colours can be objectively measured by specifying the hue, saturation and brightness values of each colour,
- As a means of reducing the large amount of data contained in the images, several binning and visualisation methods can be pursued,
- Body tone can be determined, and,
- The apparatus can be further used to assess, grade and evaluate all gemstones, including inorganic gemstones and minerals, such as, or other than, opals.
- All calibration, segmentation and histogram measurement tasks involved in image analysis are facilitated by one or more computers operated by software derived from specialised mathematical algorithms. Software also drives the operation of the camera, lighting, stage and other components of the image capture apparatus.

It will be apparent to persons skilled in the art that various modifications may be made in details of design and construction of the apparatus, and in method steps of the methods described above without departing from the scope of ambit of the invention.

For example, a useful image capture methodology is to secure the gemstone on a stationary stage (so as to eliminate any potential movement problems of the gemstone), and systematically move the at least one light source and camera to enable image capture sequences to simulate the required pitch, roll and yaw movements.

Furthermore, the apparatus may include a plurality of digital cameras and positioned lights, and all of the cameras may take images of the gemstone simultaneously, or in sequence, at predetermined angular increments during rotation of the stage.

The invention claimed is:

1. An apparatus for assessment, evaluation and grading of gemstones, comprising a stage upon which a gemstone may be supported, the stage being enclosed in a housing that is impervious to light, at least one light source located in the housing and adapted to project incident light onto the gemstone, means for rotating and tilting the stage so as to vary the orientation of the gemstone to the incident light, a digital camera located in the housing adjacent the or each light source and adapted to take images of the gemstone based on reflection and/or refraction of the incident light, and information processing means for calibrating and analyzing the images, wherein the information processing means is programmed with instruction sets for assessing one or more of colour, cut, clarity, scintillation, brilliance, lustre, dispersion and sheen, and wherein the gemstone is supported upon the stage by securing means engaging the gemstone at its bottom surface, and wherein colour assessment of the gemstone is with an instruction set for colour calibrating the images and then analysing the colour calibrated images by segmentation and histogram measurement.

2. The apparatus of claim 1 wherein the securing means is a suction cup for holding the gemstone tightly using suction from beneath the gemstone.

3. The apparatus of claim 1 wherein the stage is rotatable around 360° and tiltable around 90° by movement of a goniometer.

4. The apparatus of claim 1 wherein the information processing means is programmed with a further instruction set for controlling the camera to capture a series of images at 10° angles for 0° to 360° of rotation and at 10° angles for 90° to 0° of tilt.

5. The apparatus of claim 1 wherein the instruction set is software programmed into a personal computer.

6. The apparatus of claim 1 wherein the gemstone is an opal, and the image colour calibration and image analysis is for assessing the characteristics of flash and body tone of the opal.

7. A method for assessment, evaluation and grading of gemstones with an information processing means, including the steps of:—
   (a) colour calibrating a plurality of images of a gemstone captured by a digital camera, and
   (b) analysing the colour calibrated images by segmentation and histogram measurement.

* * * * *